(12) United States Patent
Yoneda

(10) Patent No.: US 7,569,231 B2
(45) Date of Patent: Aug. 4, 2009

(54) METHOD FOR STABILIZING OIL-BASED THICKENING GEL COMPOSITION

(75) Inventor: Tadashi Yoneda, Chiba (JP)

(73) Assignee: Showa Denko K.K., Tokyo (JP)

( * ) Notice: Subject to any disclaimer, the term of this patent is extended or adjusted under 35 U.S.C. 154(b) by 111 days.

(21) Appl. No.: 10/588,086

(22) PCT Filed: Jan. 28, 2005

(86) PCT No.: PCT/JP2005/001644

§ 371 (c)(1),
(2), (4) Date: Jul. 31, 2006

(87) PCT Pub. No.: WO2005/074881

PCT Pub. Date: Aug. 18, 2005

(65) Prior Publication Data

US 2007/0190087 A1  Aug. 16, 2007

Related U.S. Application Data

(60) Provisional application No. 60/543,400, filed on Feb. 11, 2004.

(30) Foreign Application Priority Data

Feb. 6, 2004 (JP) .............................. 2004-031145

(51) Int. Cl.
*A61K 8/64* (2006.01)
*C07K 7/06* (2006.01)

(52) U.S. Cl. ........................ 424/401; 530/300; 530/328; 530/329

(58) Field of Classification Search ........................ None
See application file for complete search history.

(56) References Cited

U.S. PATENT DOCUMENTS

| 4,767,625 A | 8/1988 | Mitsuno et al. |
| 4,883,659 A * | 11/1989 | Goodman et al. ........ 424/78.03 |
| 5,380,455 A | 1/1995 | Tsuda et al. |
| 5,583,105 A * | 12/1996 | Kovacs et al. .................. 514/11 |
| 5,928,657 A | 7/1999 | Simon |
| 6,284,268 B1 * | 9/2001 | Mishra et al. ............... 424/455 |

FOREIGN PATENT DOCUMENTS

| JP | 62-53910 A | 3/1987 |
| JP | 3-141212 A | 6/1991 |
| JP | 9-255520 A | 9/1997 |
| JP | 2000-26238 A | 1/2000 |
| JP | 2000-229816 A | 8/2000 |
| JP | 2000-239123 A | 9/2000 |
| JP | 2003-176211 A | 6/2003 |
| WO | 99/62482 A1 | 12/1999 |
| WO | WO 03/013446 A1 * | 2/2003 |

OTHER PUBLICATIONS

NPL-from Derwent document 1996-240507-same as US Patent No. 5583105.*
Tharwat Tadros, "Advances in Emulsion Science for Personal Care Applications", Journal of Cosmetic Science, Society of Cosmetic Chemists, New York, NY,, US, vol. 52, No. 2, 2001, pp. 138-154, XP001107113, ISSN 1525-7886, pp. 153, 154.
Tadashi Yoneda, et al, "Surfactin Sodium Salt: An Excellent Bio-Surfactant for Cosmetics", Caplus, vol. 29, No. 12, XP002218400, Abstract, 2001.

* cited by examiner

*Primary Examiner*—Cecilia Tsang
*Assistant Examiner*—Julie Ha
(74) *Attorney, Agent, or Firm*—Sughrue Mion, PLLC

(57) ABSTRACT

The present invention relates to (1) a stabilized oil-based thickening gel composition comprising (a) an anionic surfactant having a lipopeptide structure, (b) water and/or a polyhydric alcohol having a valence of 3 or more, (c) a tocopherol compound and (d) an oil component, (2) a method for improving storage ability of an oil-based thickening gel composition characterized by addition of (c) tocopherol compound to an oil-based thickening gel composition comprising (a) an anionic surfactant having a lipopeptide structure, (b) water and/or a polyhydric alcohol having a valence of 3 or more and (d) an oil component, and (3) a cosmetic comprising the oil-based thickening gel composition.

3 Claims, No Drawings

METHOD FOR STABILIZING OIL-BASED THICKENING GEL COMPOSITION

CROSS-REFERENCE TO RELATED APPLICATIONS

This is an application filed pursuant to 35 U.S.C. Section 111 (a) with claiming the benefit of U.S. provisional application Ser. No. 60/543,400 filed Feb. 11, 2004 under the provision of 35 U.S.C. 111 (b), pursuant to 35 U.S.C. Section 119 (e)(1).

TECHNICAL FIELD

The present invention relates to a method for improving storage stability of an oil-based thickening gel composition, an oil-based thickening gel composition stabilized by the method and cosmetic product containing the same.

Background Art

As a method for obtaining an oil gel composition, a method in which a liquid oil component is mixed with silicic acid anhydride, a method in which it is mixed with a metallic soap, a method in which it is mixed with a polyhydric alcohol and a nonionic surfactant, and the like have been so far known.

For example, JP-A-62-53910 (related document: U.S. Pat. No. 4,767,625) discloses liquid-crystalline-type cosmetics obtained from a hydrophilic nonionic surfactant, a water-soluble material having a hydroxyl group in a molecule, an oil component and water.

JP-A-3-141212 discloses non-aqueous sol cosmetics comprising low-polarity oil, a metallic soap and a nonionic surfactant. JP-A-6-48921 (U.S. Pat. No. 5,380,455) discloses a cleansing composition containing a fluoropolymer and liquid oil. JP-A-9-255520 discloses non-aqueous cosmetics comprising from 40 to 70% by mass of a polyhydric alcohol, from 10 to 50% by mass of a non-polar or low-polarity component and from 1 to 30% by mass of a hydrophilic surfactant.

JP-A-10-139627 (U.S. Pat. No. 5,928,657) discloses a transparent gel comprising a fatty phase, a carbohydrate fatty ester having 5 to 7 carbon atoms and a polyhydric alcohol. JP-A-2000-26238 discloses jelly cosmetics comprising diglycerin tetraoleate and isoparaffin having from 16 to 30 carbon atoms. JP-A-2000-229816 discloses non-solid, non-aqueous oil cosmetics comprising a dextrin fatty acid ester, a heavy liquid paraffin and an oil component which is liquid at normal temperature. JP-A-2000-239123 discloses an oil gel composition comprising an unsaturated or branched alcohol having from 12 to 30 carbon atoms, an amphoteric surfactant and water.

However, in the methods using silicic acid anhydride, a metallic soap, a nonionic surfactant and the like, these components have to be mixed in large amounts for gelation. Thus, the methods involve problems that spreadability on the skin is poor, that some users may suffer from skin irritation, that the low oil content may lead to inferior cleansing property as compared to liquid cleansing oil, and the like. In the method in which a dextrin fatty acid ester is compounded in, stability is insufficient due to easy-to-collapse gel. Accordingly, none of the conventional oil-based thickening gel compositions is satisfactory.

The present inventors found that an oil-based thickening gel composition comprising an anionic surfactant having a lipopeptide structure, water and/or a polyhydric alcohol and an oil component can be prepared, and disclosed the finding in JP-A-2003-176211.

However, in the technique, there still remains a problem that when a polyoxyethyleneglyceryl ether fatty acid ester, a polyoxyethylene sorbitol ether fatty acid ester or the like is used as an oil component, sufficient storage stability cannot be obtained.

DISCLOSURE OF THE INVENTION

An object of the present invention is to provide a method for stabilizing storage stability of an oil-based thickening gel composition which is quite low in skin irritation, can contain a large amount of oil components and is suitable for cleansing products, moist products and the like, especially an oil-based thickening gel composition containing polyoxyethyleneglyceryl ether fatty acid esters, polyoxyethylene sorbitol ether fatty acid esters and the like, an oil-based thickening gel composition stabilized by the method, and cosmetics containing the stabilized oil-based thickening gel composition.

The present inventors have assiduously conducted investigations to solve the foregoing problems, and have consequently found that when (c) a tocopherol compound is added to an oil-based thickening gel composition comprising (a) an anionic surfactant having a lipopeptide structure, (b) water and/or a polyhydric alcohol having a valence of 3 or more and (d) an oil component, storage stability is markedly improved. This finding has led to the completion of the present invention.

That is, the invention relates to the following matters.

1. An oil-based thickening gel composition comprising (a) an anionic surfactant having a lipopeptide structure, (b) water and/or a polyhydric alcohol having a valence of 3 or more, (c) a tocopherol compound and (d) an oil component.
2. The oil-based thickening gel composition as described in 1, wherein the addition amount of (c) the tocopherol compound is from 0.01 to 2% by mass based on the oil-based thickening gel composition.
3. The oil-based thickening gel composition as described in 1 or 2, wherein the amount of (a) the anionic surfactant having a lipopeptide structure is from 0.01 to 5% by mass, the amount of (b) the water and/or the polyhydric alcohol having a valence of 3 or more is from 0.01 to 70% by mass and the amount of (c) the oil component is from 30 to 99% by mass.
4. The oil-based thickening gel composition as described in 1, wherein (a) the anionic surfactant having a lipopeptide structure is surfactin represented by the following formula (1)

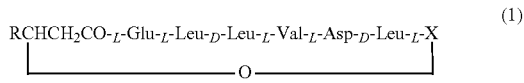

wherein X represents an amino acid residue selected from the group consisting of leucine, isoleucine, valine, glycine, serine, alanine, threonine, asparagine, glutamine, aspartic acid, glutamic acid, lysine, arginine, cysteine, methionine, phenylalanine, tyrosine, tryptophan, histidine, proline, 4-hydroxyproline and homoserine, and R represents a normal alkyl group having from 8 to 14 carbon atoms, an isoalkyl group having from 8 to 14 carbon atoms or an anteisoalkyl group having from 8 to 14 carbon atoms, its homologue, and/or salts thereof.

5. The oil-based thickening gel composition as described in 4, wherein X is leucine, isoleucine or valine.
6. The oil-based thickening gel composition as described in 4, wherein (a) the anionic surfactant having a lipopeptide structure is sodium surfactin.
7. The oil-based thickening gel composition as described in 1, wherein (d) the oil component is one or more selected from polyoxyethyleneglyceryl ether fatty acid esters and polyoxyethylene sorbitol ether fatty acid esters.
8. The oil-based thickening gel composition as described in 1, wherein (c) the tocopherol compound is one or more selected from the group consisting of α-tocopherol, β-tocopherol, γ-tocopherol, δ-tocopherol, tocopherol acetate and tocopherol succinate.
9. The oil-based thickening gel composition as described in 1, wherein the polyhydric alcohol having a valence of 3 or more is one or more selected from the group consisting of glycerin, diglycerin, polyglycerin, sorbitol, mannitol, xylitol, multitol, erythritol, pentaerythritol, glucose, saccharose, fructose, lactose, maltose, xylose and trehalose.
10. The oil-based thickening gel composition as described in 9, wherein the polyhydric alcohol having a valence of 3 or more is glycerin and/or sorbitol.
11. A method for improving storage stability of an oil-based thickening gel composition, comprising addition of (c) a tocopherol compound to an oil-based thickening gel composition comprising (a) an anionic surfactant having a lipopeptide structure, (b) water and/or a polyhydric alcohol having a valence of 3 or more and (d) an oil component.
12. The method for improving storage stability of an oil-based thickening gel composition as described in 11, wherein the addition amount of (c) the tocopherol compound is from 0.01 to 2% by mass.
13. The method for improving storage stability of an oil-based thickening gel composition as described in 11 or 12, wherein the oil-based thickening gel composition comprises from 0.01 to 5% by mass of (a) an anionic surfactant having a lipopeptide structure, from 0.01 to 70% by mass of (b) water and/or a polyhydric alcohol having a valence of 3 or more and from 30 to 99% by mass of (d) an oil component.
14. The method for improving storage stability of an oil-based thickening gel composition as described in 11, wherein (a) the anionic surfactant having a lipopeptide structure is surfactin represented by the following formula (1)

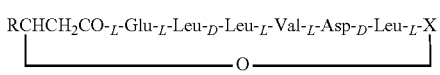

wherein X represents an amino acid residue selected from the group consisting of leucine, isoleucine, valine, glycine, serine, alanine, threonine, asparagine, glutamine, aspartic acid, glutamic acid, lysine, arginine, cysteine, methionine, phenylalanine, tyrosine, tryptophan, histidine, proline, 4-hydroxyproline and homoserine, and R represents a normal alkyl group having from 8 to 14 carbon atoms, an isoalkyl group having from 8 to 14 carbon atoms or an anteisoalkyl group having from 8 to 14 carbon atoms, its homologue, and/or salts thereof.
15. The method for improving storage stability of an oil-based thickening gel composition as described in 14, wherein X is leucine, isoleucine or valine.

16. The method for improving storage stability of an oil-based thickening gel composition as described in 14, wherein (a) the anionic surfactant having a lipopeptide structure is sodium surfactin.
17. The method for improving storage stability of an oil-based thickening gel composition as described in 11, wherein the oil component is one or more selected from polyoxyethyleneglyceryl ether fatty acid esters and polyoxyethylene sorbitol ether fatty acid esters.
18. The method for improving storage stability of an oil-based thickening gel composition as described in 11, wherein (c) the tocopherol compound is one or more selected from the group consisting of α-tocopherol, β-tocopherol, γ-tocopherol, δ-tocopherol, tocopherol acetate and tocopherol succinate.
19. A cosmetic comprising the oil-based thickening gel composition as described in any one of 1 to 10.

DETAILED DESCRIPTION OF THE INVENTION

The invention is described in detail below.

The tocopherol compound (c) used in the invention is a compound represented by the following formula (2)

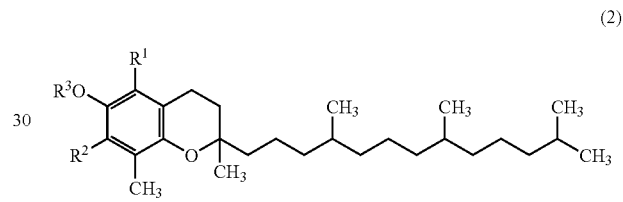

wherein $R^1$ and $R^2$ each represent a hydrogen atom or a methyl group, $R^3$ represents a hydrogen atom or a carboxylic acid residue, or a mixture containing two or more types of this compound. Of these, α-tocopherol ($R^1$=methyl group, $R^2$=methyl group and $R^3$=hydrogen atom), β-tocopherol ($R^1$=methyl group, $R^2$=H and $R^3$=hydrogen atom), γ-tocopherol ($R^1$=hydrogen atom, $R^2$=methyl group and $R^3$=hydrogen atom), δ-tocopherol ($R^1$=hydrogen atom, $R^2$=hydrogen atom and $R_3$=H), and tocopherol acetate and tocopherol succinate which are esters thereof are preferable. Especially, α-tocopherol and δ-tocopherol are preferable. The tocopherol maybe a d-isomer, an l-isomer or a dl-isomer, and the form is not particularly limited.

In the invention, as (a) the anionic surfactant having a lipopeptide structure, any anionic surfactant may be employed as long as an oil-based thickening gel composition can be prepared using the surfactant. Specifically, examples thereof include a salt of surfactin and a salt of its homologue.

Surfactin here is a compound represented by the formula (1) or a composition containing two or more types of this compound.

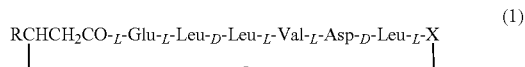

In the formula (1), X represents an amino acid residue selected from the group consisting of leucine, isoleucine, valine, glycine, serine, alanine, threonine, asparagine, glutamine, aspartic acid, glutamic acid, lysine, arginine, cysteine, methionine, phenylalanine, tyrosine, tryptophan, histidine, proline, 4-hydroxyproline and homoserine. X is preferably leucine, isoleucine or valine.

R represents a normal alkyl group having from 8 to 14 carbon atoms, an isoalkyl group having from 8 to 14 carbon atoms or an anteisoalkyl group having from 8 to 14 carbon atoms. A normal alkyl group is a linear alkyl group, an isoalkyl group has usually a structure comprising $(CH_3)_2CH-(CH_2)_n-$, and an anteisoalkyl group has a structure comprising $CH_3-CH_2-CH (CH_3)-(CH_2)_n-$.

The homologue of surfactin is a compound in which amino acids of the foregoing formula (1) are replaced with other amino acids. Specifically, compounds in which L-leucine as the second amino acid, L-valine as the fourth amino acid, and/or D-leucine as the sixth amino acid are replaced with other amino acids are mentioned as examples. However, the compound is not limited to these examples. In the present specification, "surfactin or its homologue" is sometimes referred to simply as "surfactin".

Surfactin is usually produced from a procaryote. As the procaryote, microorganisms belonging to the genus *Bacillus*, such as *Bacillus subtilis* IAM 1213 strain, IAM 1069 strain, IAM 1259 strain, IAM 1260 strain, IFO 3035 strain and ATCC 21332 strain are generally used.

Surfactin can easily be obtained by culturing the microorganisms and conducting purification. The purification is conducted, for example, by acidifying the culture solution through addition of hydrochloric acid or the like, separating surfactin precipitated by filtration, dissolving the surfactin in an organic solvent such as methanol, and then conducting ultrafiltration, activated carbon treatment, crystallization or the like as required.

The precipitation by acid addition may be changed to precipitation by addition of a calcium salt (Biochem. Bioph. Res. Commun., 31: 488-494 (1968)).

As surfactin, besides surfactin produced from the procaryote such as microorganisms of the genus *Bacillus*, surfactin obtained by other methods, for example, a chemical synthetic method can also be used.

Surfactin can be used, as is apparent from the formula (1), in the form of an inorganic salt or an organic salt. The type of metal serving as a counter ion is not particularly limited as far as the metal can form a salt with the surfactin, and examples thereof include alkali metals such as sodium, potassium and lithium, alkaline earth metals such as calcium and magnesium, and the like.

Examples of the organic salt can include trimethylamine, triethylamine, tributylamine, monoethanolamine, diethanolamine, triethanolamine, lysine, arginine, choline and the like.

Of these, sodium, potassium, monoethanolamine, diethanolamine, triethanolamine, lysine and arginine are preferable, and sodium is especially preferable.

Regarding a sodium salt of surfactin, a product sold by Showa Denko K. K. as sodium surfactin under a trade name of Aminofect (registered trademark) can be used.

The anionic surfactant having a lipopeptide structure (a), such as surfactin, its homologue and/or salts thereof, is extremely mild to the skin. Such mildness of surfactin, its homologue and/or salts thereof is assumed to be attributable to its cyclic compound structure being intricate and bulky to reduce permeability into the skin. Further, it is assumed that surfactin, its homologue and/or salts thereof brings about a masking effect of reducing skin irritation by blocking skin irritants. Accordingly, the invention provides an oil-based thickening gel composition which is extremely low in skin irritation.

A content of (a) the anionic surfactant having the lipopeptide structure in the invention is not particularly limited. It is preferably from 0.01 to 5% by mass, more preferably from 0.1 to 2% by mass. When it is less than 0.01% by mass, gelation does not proceed satisfactorily. When it is used in an amount exceeding 5% by mass, stability might be rather impaired.

The polyhydric alcohol having a valence of 3 or more used in the invention is not particularly limited, and any such a polyhydric alcohol can be used so long as they are ordinarily used in cosmetics and the oil-based thickening gel composition of the invention can thereby be prepared.

Examples of such a polyhydric alcohol include glycerin, diglycerin, polyglycerin, sorbitol, mannitol, xylitol, maltitol, erythritol, pentaerythritol, glucose, saccharose, fructose, lactose, maltose, xylose, trehalose and the like. These may be used either singly or in combination of two or more thereof.

Of these, glycerin and sorbitol are especially preferable.

A content of (b) water and/or a polyhydric alcohol having a valence of 3 or more in the oil-based thickening gel composition of the invention is preferably from 0.01 to 70% by mass, more preferably from 0.05 to 39% by mass, further preferably from 0.1 to 36% by mass based on the total amount of the composition. When it is less than 0.01% by mass, no sufficient stability can be retained. When it is used in an amount exceeding 70% by mass, the content of oil component becomes insufficient, so that the composition fails to have a gel form.

When the oil-based thickening gel composition of the invention contains water, a gel having low viscosity can be prepared. When the composition is used as a gel material of cosmetics, feeling upon use of the cosmetic can be improved. A combination of an oil phase and an aqueous phase having close refractive indexes can provide a gel having transparent appearance to improve designing property.

The oil component (d) used in the invention is not particularly limited, and materials which are ordinarily used in cosmetics can be used. Materials which are liquid or pasty at 1 atm and 25° C. are preferable, and liquid oil is preferable.

The liquid oil includes hydrocarbons, higher alcohol esters, higher fatty acid esters, triglycerides, silicone oils, animal and vegetable oils, sorbitan fatty acid esters, polyoxyethylenesorbitan fatty acid esters, polyoxyethyleneglyceryl ether fatty acid esters, polyoxyethylene sorbitol fatty acid esters, polyoxyalkylenealkyl ethers and the like. Preferable examples thereof include squalane, synthetic squalane, vegetable squalane, liquid isoparaffin, liquid paraffin, mineral oil, jojoba oil, avocado oil, almond oil, olive oil, extra virgin olive oil, sesame oil, rice bran oil, rice oil, rice germ oil, corn oil, safflower oil, soybean oil, corn oil, rapeseed oil, persic oil, palm kernel oil, palm oil, castor oil, sunflower oil, high oleic sunflower oil, grape seed oil, cottonseed oil, coconut oil, hydrogenated coconut oil, beef tallow, hardened oil, horse oil, mink oil, yolk oil, yolk fatty oil, rose hip oil, kukui nut oil, evening primrose oil, wheat germ oil, peanut oil, camellia oil, sasanqua oil, macadamia nut oil, meadowfoam seed oil, isopropyl myristate, butyl myristate, isopropyl palmitate, ethyl stearate, butyl stearate, ethyl oleate, ethyl linoleate, isopropyl linoleate, cetyl caprylate, hexyl laurate, isooctyl myristate, decyl myristate, decyl oleate, oleyl oleate, cetyl ricinoleate, isostearyl laurate, isotridecyl myristate, isocetyl myristate, isostearyl myristate, octyldodecyl myristate, 2-ethylhexyl palmitate, isocetyl palmitate, isostearyl palmitate, 2-ethylhexyl stearate, isocetyl stearate, isodecyl oleate, octyldodecyl oleate, octyldodecyl ricinoleate, ethyl isostearate, isopropyl isostearate, cetyl 2-ethylhexanoate, cetostearyl 2-ethylhexanoate, stearyl 2-ethylhexanoate, hexyl isostearate, ethylene glycol dioctanoate, ethylene glycol dioleate, propylene glycol dicaprylate, propylene glycol di(capryl-caprate), propylene glycol dicaprate, propylene glycol dioleate, neopentyl glycol dicaprate, neopentyl glycol dioctanoate, glyceryl tricaprylate, glyceryl tri-2-ethylhexanoate, glyceryl tri (caprylcaprate), glyceryl triisopalmitate, glyceryl triisostearate, trimethylolpropane tri-2-ethylhexanoate, trimethylolpropane triisostearate, pentaerythrityl tetra-2-ethylhexanoate, pentaerythrityl tetraisostearate, octyldodecyl neopentanoate, isocetyl octanoate, isostearyl octanoate, 2-ethylhexyl isopelargonate, hexyldecyl dimethyloctanoate, octyldodecyl dimethyloctanoate, 2-ethylhexyl isopalmitate, isocetyl isostearate, isostearyl isostearate, octyldodecyl isostearate, lauryl lactate, myristyl lactate, octyldodecyl lactate, triethyl citrate, acetyltriethyl citrate, acetyltributyl citrate, trioctyl citrate, triisocetyl citrate, trioctyldodecyl citrate, diisostearyl malate, 2-ethylhexyl hydroxystearate, di-2-ethylhexyl succinate, diisopropyl adipate, diisobutyl adipate, dioctyl adipate, diheptylundecyl adipate, diethyl sebacate, diisopropyl sebacate, dioctyl sebacate, isocetyl 12-stearoylhydroxystearate, stearyl 12-stearoylhydroxystearate, isostearyl 12-stearoylhydroxystearate, polyoxyethylene (3) polyoxypropylene (1) cetyl ether acetate, polyoxyethylene (3) polyoxypropylene (1) isocetyl ether acetate, isononyl isononanoate, octyl isononanoate, tridecyl isononanoate, isotridecyl isononanoate, polyoxyethylene (3) glyceryl triisostearate, polyoxyethylene (5) glyceryl triisostearate, polyoxyethylene (10) glyceryl triisostearate, polyoxyethylene (20) glyceryl triisostearate, polyoxyethylene (30) glyceryl triisostearate, polyoxyethylene (40) glyceryl triisostearate, polyoxyethylene (50) glyceryl triisostearate, polyoxyethylene (60) glyceryl triisostearate, polyoxyethylene (3) glyceryl isostearate, polyoxyethylene (5) glyceryl isostearate, polyoxyethylene (6) glyceryl isostearate, polyoxyethylene (8) glyceryl isostearate, polyoxyethylene (10) glyceryl isostearate, polyoxyethylene (15) glyceryl isostearate, polyoxyethylene (20) glyceryl isostearate, polyoxyethylene (25) glyceryl isostearate, polyoxyethylene (30) glyceryl isostearate, polyoxyethylene (40) glyceryl isostearate, polyoxyethylene (50) glyceryl isostearate, polyoxyethylene (60) glyceryl isostearate, polyoxyethylene (3) glyceryl tristearate, polyoxyethylene (4) glyceryl tristearate, polyoxyethylene (5) glyceryl tristearate, polyoxyethylene (6) glyceryl tristearate, polyoxyethylene (10) glyceryl tristearate, polyoxyethylene (20) glyceryl tristearate, polyoxyethylene (4) glyceryl distearate, polyoxyethylene (3) glyceryl trioleate, polyoxyethylene (5) glyceryl trioleate, polyoxyethylene (10) glyceryl trioleate, polyoxyethylene (20) glyceryl trioleate, polyoxyethylene (30) glyceryl trioleate, polyoxyethylene (40) glyceryl trioleate, polyoxyethylene (50) glyceryl trioleate, polyoxyethylene (60) glyceryl trioleate, polyoxyethylene sorbitol monolaurate, polyoxyethylene (40) sorbitol oleate, polyoxyethylene (4) sorbitol tetraoleate, polyoxyethylene (3) sorbitol tristearate, polyoxyethylene (30) sorbitol tetraoleate, polyoxyethylene (40) sorbitol tetraoleate, polyoxyethylene (60) sorbitol tetraoleate, polyoxyethylene (3) sorbitol isostearate, polyoxyethylene (40) sorbitol oleate, polyoxyethylene (60) sorbitol tetrastearate, polyoxyethylene (6) sorbitol hexaoleate, polyoxyethylenesorbitol hexastearate, polyoxyethylene (40) sorbitol pentaoleate, clove oil, orange oil, orange peel oil, dicapryl carbonate, methylpolysiloxane, methylphenylpolysiloxane, methylhydrodienepolysiloxane, methylcyclopolysiloxane, octamethylcyclotetrasiloxane, decamethylcyclopentasiloxane, dodecamethylcyclohexasiloxane, octamethyltrisiloxane, decamethyltetrasiloxane, tetradecamethylhexasiloxane, polymeric methylpolysiloxane, dimethylsiloxane.methyl(polyoxyethylene)siloxane.methyl (polyoxypropylene) siloxane copolymer, dimethylsiloxane.methyl (polyoxyethylene)siloxane copolymer, dimethylsiloxane·methyl (polyoxypropylene) siloxane copolymer, dimethylsiloxane·methylcetyloxysiloxane copolymer, dimethylsiloxane·methylstearoxysiloxane copolymer, polyether-modified silicone, alcohol-modified siloxane, alkyl-modified silicone, amino-modified silicone, and the like.

The stabilizing method of the invention provides especially preferable effects when using polyoxyethyleneglyceryl ether fatty acid esters and polyoxyethylene sorbitol ether fatty acid esters, namely, polyoxyethylene (3) glyceryl triisostearate, polyoxyethylene (5) glyceryl triisostearate, polyoxyethylene (10) glyceryl triisostearate, polyoxyethylene (20) glyceryl triisostearate, polyoxyethylene (30) glyceryl triisostearate, polyoxyethylene (40) glyceryl triisostearate, polyoxyethylene (50) glyceryl triisostearate, polyoxyethylene (60) glyceryl triisostearate, polyoxyethylene (3) glyceryl isostearate, polyoxyethylene (5) glyceryl isostearate, polyoxyethylene (6) glyceryl isostearate, polyoxyethylene (8) glyceryl isostearate, polyoxyethylene (10) glyceryl isostearate, polyoxyethylene (15) glyceryl isostearate, polyoxyethylene (20) glyceryl isostearate, polyoxyethylene (25) glyceryl isostearate, polyoxyethylene (30) glyceryl isostearate, polyoxyethylene (40) glyceryl isostearate, polyoxyethylene (50) glyceryl isostearate, polyoxyethylene (60) glyceryl isostearate, polyoxyethylene (3) glyceryl tristearate, polyoxyethylene (4) glyceryl tristearate, polyoxyethylene (5) glyceryl tristearate, polyoxyethylene (6) glyceryl tristearate, polyoxyethylene (10) glyceryl tristearate, polyoxyethylene (20) glyceryl tristearate, polyoxyethylene (4) glyceryl distearate, polyoxyethylene (3) glyceryl trioleate, polyoxyethylene (5) glyceryl trioleate, polyoxyethylene (10) glyceryl trioleate, polyoxyethylene (20) glyceryl trioleate, polyoxyethylene (30) glyceryl trioleate, polyoxyethylene (40) glyceryl trioleate, polyoxyethylene (50) glyceryl trioleate, polyoxyethylene (60) glyceryl trioleate, polyoxyethylene sorbitol monolaurate, polyoxyethylene (40) sorbitol oleate, polyoxyethylene (4) sorbitol tetraoleate, polyoxyethylene (3) sorbitol tristearate, polyoxyethylene (30) sorbitol tetraoleate, polyoxyethylene (40) sorbitol tetraoleate, polyoxyethylene (60) sorbitol tetraoleate, polyoxyethylene (3) sorbitol isostearate, polyoxyethylene (40) sorbitol oleate, polyoxyethylene (60) sorbitol tetrastearate, polyoxyethylene (6) sorbitol hexaoleate, polyoxyethylene sorbitol hexastearate and polyoxyethylene (40) sorbitol pentaoleate.

These may be used either singly or in combination of two or more thereof.

A content of (d) the oil component in the oil-based thickening gel composition of the invention is from 30 to 99% by mass, more preferably from 50 to 95% by mass. When it is less than 30% by mass, no gel is provided, and when it exceeds 99% by mass, no sufficient stability can be maintained.

The oil-based thickening gel composition of the invention can contain an ultraviolet absorber. The ultraviolet absorber here refers to a material which is ordinarily used in a sun screen product or the like, and which can reduce ultraviolet A wave, ultraviolet B wave or both of them to decrease hazardous activity of ultraviolet light to the skin.

Examples of such an ultraviolet absorber include p-aminobenzoic acid and p-aminobenzoic acid derivatives such as glyceryl p-aminobenzoate, amyl p-N,N-dimethylaminobenzoate and 2-ethylhexyl p-N,N-dimethylaminobenzoate; cinnamic acid derivatives such as methyl 2,4-diisopropylcinnamate, ethyl 2,4-diisopropylcinnamate, potassium p-methoxycinnamate, sodium p-methoxycinnamate, isopropyl p-methoxycinnamate, 2-ethylhexyl p-methoxycinnamate, 2-ethoxyethyl p-methoxycinnamate and ethyl p-ethoxycinnamate; benzophenone derivatives such as 2,4-dihydroxybenzophenone, 2,2',4,40 -tetrahydroxybenzophenone, 2-hydroxy-4-methoxy-5-sulfobenzophenone sodium, 2-hydroxy-4-methoxybenzophenone-5-sulfonic acid, 2-hydroxy-4-methoxybenzophenone, 2,2'-dihydroxy-4,4'-dimethoxybenzophenone and 2,2'-dihydroxy-4,4'-dimethoxy-5-sulfobenzophenone sodium; salicylic acid derivatives such as 2-ethylhexyl salicylate, phenyl salicylate and 3,3, 5-trimethylcyclohexyl salicylate; 2-(2'-hydroxy-5'-methoxyphenyl)benzotriazole, 4-tert-butyl-4'-methoxybenzoylmethane, and the like.

Of these, compounds which are solid at normal temperature can be used by being dissolved or dispersed in liquid oil. Compounds which are liquid or pasty at normal temperature can be used themselves as liquid oils or by being mixed with other liquid oils. Among compounds which can be used themselves as liquid oils, 2-ethylhexyl p-methoxycinnamate or a 2-ethylhexyl p-methoxycinnamate solution of 4-tert-butyl-4'-methoxybenzoylmethane is especially preferable.

The oil-based thickening gel composition of the invention may contain an antioxidant and a perfume. Materials which are solid at normal temperature can be used by being dissolved or dispersed in liquid oil. Materials which are liquid or pasty at normal temperature may be used themselves as liquid oils or by being mixed with other liquid oils. Examples of the antioxidant which can be used include tocopherol, tocopherol acetate and vitamin A (for example, retinoic acid, retinoic acid ester, retinol and retinoid).

The oil-based thickening gel composition of the invention can be prepared, for example, by dissolving (a) an anionic surfactant having a lipopeptide structure in (b) a polyhydric alcohol having a valence of 3 or more and/or water and adding (d) an oil component in small portions with stirring. When a polyhydric alcohol and water are used in combination, water may be added after addition of the oil component.

The oil component(d) may be added in predetermined amounts (divided addition) or added continuously (continuous addition).

In case of the divided addition, 60% by mass or less, preferably 30% by mass or less, more preferably 10% by mass or less based on the amount of (b) the water and/or the polyhydric alcohol having a valence of 3 or more which has been added is added at a time, and the mixture is stirred to homogenize it. This procedure involving addition and stirring is repeated to add a necessary amount thereof.

In the continuous addition, an addition rate is 60% by mass or less per minute, preferably 30% by mass or less per minute, more preferably 10% by mass or less per minute based on the amount of (b)the water and/or the polyhydric alcohol having a valence of 3 or more which has been added.

When other components are added, they may be added by any method among a method where the other components are added before addition of (d) the oil component, a method where the other components are added in a dissolved or dispersed state in (d) the oil component, a method where the other components are added after addition of the total amount of (d) the oil component and a method where the other components are added during addition of (d) the oil component. The water and/or the polyhydric alcohol having a valence of 3 or more (b) may be added such that the total amount thereof is added at the beginning, or a part of the addition amount thereof is first added and the remainder is later added.

In the invention, an emulsion composition extremely excellent in stability and suitable for cosmetics such as a cream and a lotion can be obtained by adding water to the oil-based thickening gel composition. A process for preparing an emulsion composition using such an oil-based thickening gel composition and the resulting emulsion composition are also included in the invention.

The oil-based thickening gel composition of the invention can be prepared as a composition having transparent appearance.

The word "transparent" here means that letters in a newspaper which is put on an opposite side to a transparent vial 30 mm in diameter with the oil-based thickening gel composition filled can be read through the vial.

The oil-based thickening gel composition having the transparent appearance can be prepared such that when refractive indexes $n^D_{20}$ of an oil phase and an aqueous phase contained therein are measured according to a method of JIS K 0062, a difference in $n^D_{20}$ of these phases is less than 0.01, preferably less than 0.005.

The oil-based thickening gel composition of the invention is preferably used in cosmetics and the like. It can be used in skin care products such as a cream, a lotion, a cleansing jelly and a cleansing cream; make-up products such as a foundation, an eye shadow, a lip color and a lip gloss; hair care products such as a hair cream, a styling jelly and a hair wax; wash products such as a shampoo, a rinse, a hand soap, a body soap and a face wash foam, and the like. These cosmetics are also included in the invention.

When the oil-based thickening gel composition is used in cosmetics, arbitrary components which are ordinarily used in cosmetics can be incorporated.

Examples of such components include hydrocarbons such as vaseline and microcrystalline wax; esters such as octyldodecyl myristate and isopropyl myristate, triglycerides such as glyceryl triisooctanoate and olive oil; silicone oils such as methylphenylpolysiloxane and methylpolysiloxane; higher alcohols such as cetanol and behenyl alcohol, fatty acids such as stearic acid and oleic acid; polyhydric alcohols such as glycerin, 1,3-butanediol and propylene glycol; lower alcohols such as ethanol and isopropyl alcohol; a nonionic surfactant, an anionic surfactant, a cationic surfactant, an amphoteric surfactant, a thickener, an ultraviolet absorber, an antioxidant, an emollient, an emulsifier, a solubilizer, an anti-inflammatory agent, a humectant, an antiseptic, a disinfectant, a pH adjustor, a dye, a perfume, a powder, water and the like.

The cosmetic of the invention may further contain existing raw materials for cosmetics in a concentration generally employed. For example, all raw materials for cosmetics are available which are described in Keshohin Genryo Kijun Dainihan Chukai, compiled by Nihon Koteisho Kyokai, 1984 (Yakuji Nipposha), Keshohin Genryo Kijungai Seibun Kikaku, supervised by Inspection Section, Pharmaceutical Affairs Bureau, Ministry of Health and Welfare, 1993 (Yakuji Nipposha), Keshohin Genryo Kijungai Seibun Kikaku Tsuiho, supervised by Inspection Section, Pharmaceutical Affairs Bureau, Ministry of Health and Welfare, 1993 (Yakuji Nipposha), Keshohin Shubetsu Kyoka Kijun, supervised by Inspection Section, Pharmaceutical Affairs Bureau, Ministry of Health and Welfare, 1993 (Yakuji Nipposha), Keshohin Genryo Jiten, 1991 (Nikko Chemicals) and the like.

In the cosmetic of the invention, nonionic surfactants, higher fatty acids and higher alcohols are used as preferable optional components. Of these, stearic acid and behenyl alcohol are preferable. The content thereof is preferably from 0. 01 to 10% by mass, more preferably from 0. 1 to 5% by mass based on the total amount of the cosmetic.

The thus-obtained cosmetic of the invention is free from skin irritation, and quite excellent as a cleansing product, a humectant, a cream, a lotion and the like.

BEST MODE FOR CARRYING OUT THE INVENTION

The invention is illustrated more specifically by referring to Examples. However, the invention is not limited by these Examples. As glycerin described below, a product having a concentration of 98% by mass or more was used. As sodium surfactin, Aminofect (registered trademark) manufactured by Showa Denko K. K. was used. "%" is % by mass.

EXAMPLES 1 TO 14 AND COMPARATIVE EXAMPLES 1 TO 14

Oil-based thickening gel compositions of Examples 1 to 14 and Comparative Examples 1 to 14 were prepared according to the following process by mixing an anionic surfactant (sodium surfactin) having a lipopeptide structure, a polyhydric alcohol (glycerin), an oil component (polyoxyethylene (20) glyceryl triisostearate, polyoxyethylene (30) sorbitol tetraoleate, squalane, glycerin tri-2-ethylhexanoate and glycerin tri(caprylcaprate)), tocopherol compounds (α-tocopherol, δ-tocopherol and tocopherol acetate) and water in mixing amounts (% by mass) shown in Table 1.

Preparation Process:

Sodium surfactin was dissolved in glycerin, and the components except water were added thereto in small portions. The mixture was stirred until a uniform solution was formed. Further, water was added, and the resulting mixture was stirred until a uniform solution was formed.

A test for storage stability was performed using the resulting compositions. In the test for storage stability, the sample was put into a glass bottle, and allowed to stand at 50° C. for 1 week and 2 months. Then, the condition was observed. A condition in which change such as separation was observed was expressed by "x", and a condition in which no change was observed was expressed by "o". The results are shown in Table 1.

TABLE 1

| | | Example No. | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| A | Sodium surfactin | 1.0 | 1.0 | 1.0 | 1.0 | 0.7 | 0.7 | 0.7 | 0.9 | 0.9 | 0.9 | 0.1 | 5.0 | 0.9 | 0.9 |
| | Glycerin | 24.5 | 24.5 | 24.5 | 24.5 | 29.5 | 31.5 | 34.5 | 37.4 | 37.4 | 37.4 | 24.3 | 24.5 | 37.6 | 37.6 |
| B | Polyoxyethylene (20) glyceryl triisostearate | 4.7 | 4.7 | 4.7 | 4.7 | 15.0 | 8.0 | 5.0 | | | | 4.7 | 4.7 | 0.1 | |
| | Polyoxyethylene (30) sorbitol tetraoleate | | | | | | | | 13.0 | 17.5 | 1.5 | | | | 0.1 |
| | Squalane | | | | | | | | 33.0 | 29.5 | 41.9 | | | 42.8 | 42.8 |
| | Glycerin tri-2-ethylhexanoate | 65.3 | | | | 50.3 | 55.3 | 55.3 | 9.9 | 8.9 | 12.5 | 66.0 | 61.35 | 12.8 | 12.8 |
| | Glycerin tri(capryl•caprate) | | 65.3 | 65.3 | 65.3 | | | | | | | | | | |
| | α-Tocopherol | | 0.1 | | | | | | 0.2 | | | | | 0.2 | |
| | δ-Tocopherol | 0.1 | | 0.1 | | 0.1 | 0.1 | 0.1 | | 0.2 | | 0.5 | 0.05 | | |
| | Tocopherol acetate | | | | 0.1 | | | | | | 0.2 | | | | 0.2 |
| C | Water | 4.4 | 4.4 | 4.4 | 4.4 | 4.4 | 4.4 | 4.4 | 5.6 | 5.6 | 5.6 | 4.4 | 4.4 | 5.6 | 5.6 |
| Total | | 100 | 100 | 100 | 100 | 100 | 100 | 100 | 100 | 100 | 100 | 100 | 100 | 100 | 100 |
| Eval. | Storage Stability 50° C. 1 week | o | o | o | o | o | o | o | o | o | o | o | o | o | o |
| | Storage Stability 50° C. 2 months | o | o | o | o | o | o | o | o | o | o | o | o | o | o |

| | | Comparative Example No. | | | | | | | | | | | | | |
|---|---|---|---|---|---|---|---|---|---|---|---|---|---|---|---|
| | | 1 | 2 | 3 | 4 | 5 | 6 | 7 | 9 | 9 | 10 | 11 | 12 | 13 | 14 |
| A | Sodium surfactin | 1.0 | 1.0 | 1.0 | 1.0 | 0.7 | 0.7 | 0.7 | 0.9 | 0.9 | 0.9 | 0.1 | 5.0 | 0.9 | 0.9 |
| | Glycerin | 24.5 | 24.5 | 24.5 | 24.5 | 29.5 | 31.5 | 34.5 | 37.4 | 37.4 | 37.4 | 24.3 | 24.5 | 37.6 | 37.6 |
| B | Polyoxyethylene (20) glyceryl triisostearate | 4.7 | 4.7 | 4.7 | 4.7 | 15.0 | 8.0 | 5.0 | | | | 4.7 | 4.7 | 0.1 | |
| | Polyoxyethylene (30) sorbitol tetraoleate | | | | | | | | 13.0 | 17.5 | 1.5 | | | | 0.1 |
| | Squalane | | | | | | | | 33.2 | 29.7 | 42.1 | | | 43.0 | 43.0 |
| | Glycerin tri-2-ethylhexanoate | 65.4 | | | | 50.4 | 55.4 | 55.4 | 9.9 | 8.9 | 12.5 | 66.5 | 61.4 | 12.8 | 12.8 |
| | Glycerin tri(capryl•caprate) | | 65.4 | 65.4 | 65.4 | | | | | | | | | | |
| | α-Tocopherol | | | | | | | | | | | | | | |
| | δ-Tocopherol | | | | | | | | | | | | | | |
| | Tocopherol acetate | | | | | | | | | | | | | | |
| C | Water | 4.4 | 4.4 | 4.4 | 4.4 | 4.4 | 4.4 | 4.4 | 5.6 | 5.6 | 5.6 | 4.4 | 4.4 | 5.6 | 5.6 |
| Total | | 100 | 100 | 100 | 100 | 100 | 100 | 100 | 100 | 100 | 100 | 100 | 100 | 100 | 100 |
| Eval. | Storage Stability 50° C. 1 week | o | o | o | o | o | o | o | o | o | o | o | o | o | o |
| | Storage Stability 50° C. 2 months | X | X | X | X | X | X | X | X | X | X | X | X | X | X |

As is apparent from Table 1, the oil-based thickening gel compositions of the invention (Examples 1 to 14) were superior to those of Comparative Examples 1 to 14 in storage stability.

EXAMPLE 15

Cleansing Product

A cleansing product was prepared by the following process according to a recipe shown in Table 2. Process:

Sodium surfactin was dissolved in glycerin, and the components except water were added thereto in small portions. The mixture was stirred until a uniform solution was formed. Further, water was added thereto, and the resulting mixture was stirred until a uniform solution was formed.

TABLE 2

| Components | Mass % |
|---|---|
| Sodium Surfactin | 1 |
| Glycerin | 24.5 |
| Polyoxyethylene (20) glyceryl triisostearate | 4.7 |
| Glycerin tri-2-ethylhexanoate | 35.4 |
| Glycerin tri(capryl•caprate) | 30 |
| δ-Tocopherol | 0.1 |
| Perfume | 0.02 |
| Purified water | balance |

A test for storage stability was performed in the foregoing manner using the resulting cleansing product. Consequently, excellent storage stability was exhibited. The resulting cleansing product was free from irritation, had smooth feel in use, and was excellent in cleansing property and rinsing property.

EXAMPLE 16

Moist product

A moist product was prepared by the following process according to a recipe shown in Table 3. Process:

Sodium surfactin was dissolved in glycerin, and the components except water were added thereto in small portions. The mixture was stirred until a uniform solution was formed. Further, water was added thereto, and the resulting mixture was stirred until a uniform solution was formed.

TABLE 3

| Components | Mass % |
|---|---|
| Sodium Surfactin | 0.7 |
| Glycerin | 34.5 |
| Squalane | 55.3 |
| Glycerin tri(capryl•caprate) | 6.4 |
| δ-Tocopherol | 0.1 |
| Perfume | 0.02 |
| Purified water | balance |

A test for storage stability was performed in the foregoing manner using the resulting moist product. Consequently, excellent storage stability was exhibited. The resulting moist product was free from irritation, had smooth feel in use, and was excellent in moistening property.

INDUSTRIAL APPLICABILITY

According to the invention, the storage stability of the oil-based thickening gel composition can remarkably be improved. When this composition is used as cosmetic, the stability is provided, the skin irritation is quite low, and the feel in use is excellent. When it is used as a moist product, the product excellent in moistening property can be provided, and when it is used as a cleansing product, the product good in cleansing property and rinsing property can be provided.

The invention claimed is:

1. A method for improving storage stability of an oil-based thickening gel composition, comprising adding (c) a tocopherol compound to an oil-based thickening gel composition comprising (a) an anionic surfactant having a lipopeptide structure, (b) water and/or a polyhydric alcohol having a valence of 3 or more and (d) from 30 to 99% by mass of an oil component being one or more selected from polyoxyethyleneglyceryl ether fatty acid esters and polyoxyethylene sorbitol ether fatty acid esters, and wherein (a) the anionic surfactant having a lipopeptide structure is surfactin represented by the following formula (1)

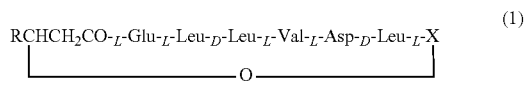

and/or salts thereof, wherein R is isoalkyl group having 11 carbon atoms, X is leucine, the polyhydric alcohol is water and glycerin, the tocopherol compound is δ-tocopherol and the oil component is polyoxyethylene (20) glyceryl triiostearate and glycerin tri-2-ethylhexanoate, and wherein the storage stability comprises preventing separation of the composition.

2. A method for improving storage stability of an oil-based thickening gel composition, comprising adding (c) a tocopherol compound to an oil-based thickening gel composition comprising (a) an anionic surfactant having a lipopeptide structure, (b) water and/or a polyhydric alcohol having a valence of 3 or more and (d) from 30 to 99% by mass of an oil component being one or more selected from polyoxyethyleneglyceryl ether fatty acid esters and polyoxyethylene sorbitol ether fatty acid esters, and wherein (a) the anionic surfactant having a lipopeptide structure is surfactin represented by the following formula (1)

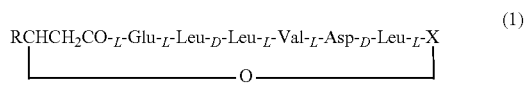

and/or salts thereof, wherein component (a) is surfactin of formula (1) in which R is isoalkyl group having 11 carbon atoms and X is leucine, component (b) is water and glycerin, component (c) is δ-tocopherol and component (d) is polyoxyethylene (20) glyceryl triiostearate and glycerin tri-2-ethylhexanoate, and wherein the storage stability comprises preventing separation of the composition.

3. The method for improving storage stability of an oil-based thickening gel composition as claimed in claim 2, wherein the surfactin is sodium surfactin.

* * * * *